(12) United States Patent
Chowhan et al.

(10) Patent No.: US 7,329,411 B2
(45) Date of Patent: *Feb. 12, 2008

(54) OPHTHALMIC COMPOSITIONS CONTAINING A SYNERGISTIC COMBINATION OF THREE POLYMERS

(75) Inventors: Masood A. Chowhan, Arlington, TX (US); Huagang Chen, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/757,494

(22) Filed: Jun. 4, 2007

(65) Prior Publication Data

US 2007/0231294 A1 Oct. 4, 2007

Related U.S. Application Data

(63) Continuation of application No. 10/863,172, filed on Jun. 8, 2004, now Pat. No. 7,244,440.

(60) Provisional application No. 60/478,713, filed on Jun. 13, 2003.

(51) Int. Cl.
*A61K 31/70* (2006.01)
*A61K 31/715* (2006.01)

(52) U.S. Cl. ............... 424/410; 424/78.37; 424/80; 514/652; 514/913

(58) Field of Classification Search .......... 424/78, 424/80, 180; 514/913, 914
See application file for complete search history.

(56) References Cited

U.S. PATENT DOCUMENTS

| | | | | |
|---|---|---|---|---|
| 3,355,336 A | | 11/1967 | Lyerly ................. 149/60 |
| 4,039,662 A | * | 8/1977 | Hecht et al. ............. 514/59 |
| 4,136,173 A | | 1/1979 | Pramoda et al. ........... 424/177 |
| 4,343,787 A | * | 8/1982 | Katz ..................... 424/428 |
| 4,767,463 A | | 8/1988 | Brode et al. ............. 106/162 |
| 5,075,104 A | * | 12/1991 | Gressel et al. .......... 424/78.04 |
| 5,368,843 A | | 11/1994 | Rennie .................. 424/49 |
| 5,652,272 A | | 7/1997 | Ogawa et al. ............ 514/652 |
| 5,939,485 A | | 8/1999 | Bromberg et al. ......... 524/556 |
| 6,316,506 B2 | | 11/2001 | Asgharian .............. 514/839 |
| 6,403,609 B1 | * | 6/2002 | Asgharian .............. 514/310 |
| 6,486,138 B1 | | 11/2002 | Asgharian et al. ......... 514/54 |
| 6,583,124 B2 | | 6/2003 | Asgharian .............. 514/54 |
| 7,001,615 B1 | | 2/2006 | Singh et al. ............ 424/488 |
| 7,244,440 B2 | | 7/2007 | Chowhan et al. ......... 424/401 |
| 2003/0232089 A1 | | 12/2003 | Singh et al. ............ 424/488 |
| 2004/0253280 A1 | | 12/2004 | Chowhan et al. ........ 424/400 |
| 2005/0013854 A1 | | 1/2005 | Mannino et al. ......... 424/450 |
| 2007/0128156 A1 | | 6/2007 | Chowhan et al. ....... 424/78.37 |
| 2007/0128288 A1 | | 6/2007 | Chowhan et al. ......... 424/488 |

FOREIGN PATENT DOCUMENTS

| | | | |
|---|---|---|---|
| WO | WO 91/19481 | | 12/1991 |
| WO | WO 92/00707 | | 1/1992 |
| WO | WO 93/17664 | | 9/1993 |
| WO | WO 9317664 | * | 9/1993 |
| WO | WO 99/06023 | | 2/1999 |
| WO | WO 02/49615 | | 6/2002 |
| WO | WO 03/059391 | | 7/2003 |

OTHER PUBLICATIONS

Arbuckle et al., "Stabilizers and Emulsifiers," *Ice Cream*, Avi Publishing Co. 1986, Chapter 6, pp. 84-94.
Charoo et al., Preparation of In Situ-Forming Ophthalmic Gels of Ciprofloxacin Hydrochloride for the Treatment of Bacterial Conjunctivitis In Vitro and In Vivo Studies, *J. Pharmaceutical Sciences*, vol. 92(2), pp. 407-413 (2003).
Goldstein et al., Guar Gum, *Industrial Gums Polysaccharides and Their Derivatives*, 2nd Edition, Academic Press, Chapter XIV, pp. 303-321 (1973).
Heyne et al., "Chemical Composition and Properties of Guar Polysaccharides," *J. American Chemical Society*, vol. 70, pp. 2249-2252 (1948).
Rocks et al., "Xanthan Gum," *Food Technology*, vol. 25, pp. 22-29, (1971).
Hoyt et al., "Friction Reduction as an Estimator of Molecular Weight," *Polymer Letters*, vol. 4, pp. 713-716 (1966).
Carbopol® Product Brochure, B.F. Goodrich (1994).

* cited by examiner

*Primary Examiner*—Michael G. Hartley
*Assistant Examiner*—Jagadishwar Samala
(74) *Attorney, Agent, or Firm*—Patrick M. Ryan

(57) ABSTRACT

Ophthalmic compositions suitable for use as artificial tears or as vehicles for ophthalmic drugs are disclosed. The compositions contain a combination of three polymers that have a synergistic effect on viscosity.

5 Claims, 1 Drawing Sheet

OPHTHALMIC COMPOSITIONS CONTAINING A SYNERGISTIC COMBINATION OF THREE POLYMERS

This application is a continuation application of U.S. Ser. No. 10/863,172, filed Jun. 8, 2004, now U.S. Pat. No. 7,244,440 which claims priority to U.S. Provisional Application Ser. No. 60/478,713, filed Jun. 13, 2003.

BACKGROUND OF THE INVENTION

1. Field of the Invention

The present invention relates to pharmaceutical compositions. In particular, this invention relates to topically administrable ophthalmic compositions that contain three polymeric components.

2. Description of Related Art

The use of polymeric ingredients in topically administrable ophthalmic compositions is well known. Polymeric ingredients are typically used in suspension compositions as physical stability aids, helping to keep the insoluble ingredients suspended or easily redispersible. In solution compositions, polymeric ingredients are typically used to increase the composition's viscosity.

Many polymers have been used in topically administrable ophthalmic compositions. Included among these are cellulosic polymers, such as hydroxypropyl methylcellulose, hydroxyethyl cellulose, and ethylhydroxyethyl cellulose. Also included are synthetic polymers, such as carboxyvinyl polymers and polyvinyl alcohol. Still others include polysaccharides such as xanthan gum, guar gum, and dextran.

Combinations of polymers have also been used in ophthalmic compositions. Certain combinations of polymers are known to provide synergistic effects on viscosity and, in some cases, even a phase transition from a liquid to a gel. For example, U.S. Pat. No. 4,136,173 discloses ophthalmic compositions containing a combination of xanthan gum and locust bean gum.

One approach to achieving a target viscosity in a topically administrable ophthalmic composition might involve simply adding a sufficient amount of one polymeric ingredient. Often, however, it is desirable to minimize the total amount of polymeric additives in topically administrable ophthalmic compositions. A mixed polymer system containing more than one polymer can significantly enhance the viscosity and lubrication property of a composition while minimizing total polymer concentration and cost of materials.

SUMMARY OF THE INVENTION

The present invention is directed toward ophthalmic compositions that contain three polymeric components. The compositions contain hydroxypropyl methylcellulose and a combination of two polymers selected from the group of combinations consisting of guar gum and a carboxyvinyl polymer; guar gum and hydroxyethyl cellulose; guar gum and dextran; hydroxyethyl cellulose and a carboxyvinyl polymer; and dextran and a carboxyvinyl polymer. The compositions are useful as artificial tear products, but can also serve as vehicles for delivering ophthalmic drugs.

The present invention is based upon the finding that the specified combinations of three polymers have a synergistic effect on viscosity.

DETAILED DESCRIPTION OF THE INVENTION

Figure 1:
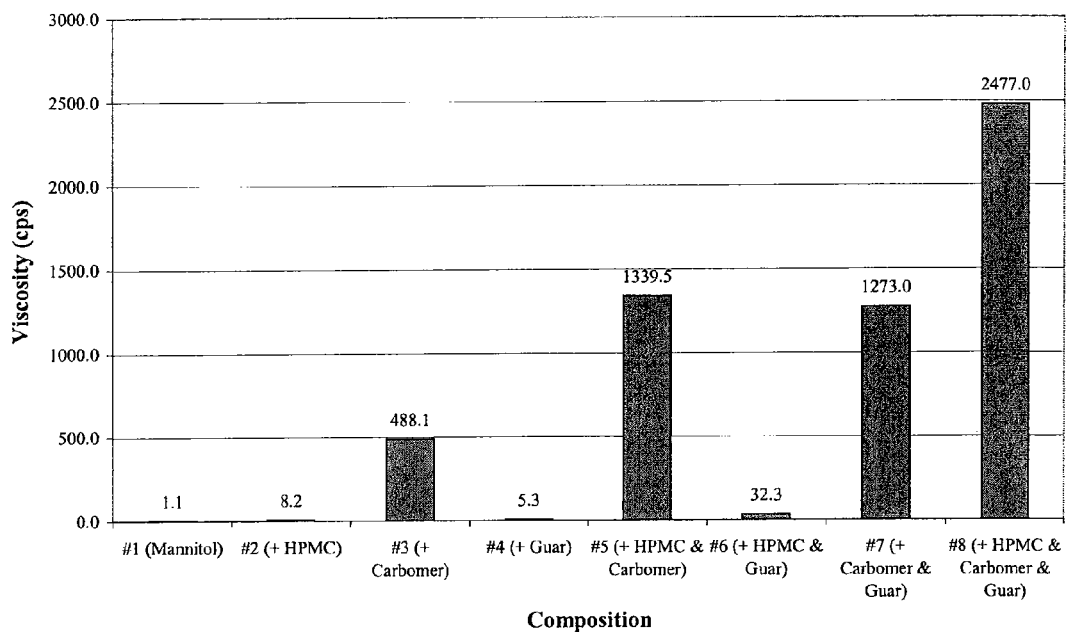
FIG. 1 shows the viscosity for each of Compositions 1-8 (Example 2), demonstrating the remarkable synergy among the three polymer system: hydroxypropyl methylcellulose, guar gum and carboxyvinyl polymer.

Unless otherwise indicated, all ingredient concentrations are listed as a weight/volume percentage basis (% w/v).

The ophthalmic compositions of the present invention are aqueous compositions that include a combination of three polymeric ingredients: hydroxypropyl methylcellulose ("HPMC") and a combination of two polymers selected from the group of combinations consisting of guar gum ("Guar") and a carboxyvinyl polymer ("carbomer"); Guar and hydroxyethyl cellulose ("HEC"); Guar and dextran; HEC and carbomer; and dextran and carbomer. All of these types of polymers are known and have been used in ophthalmic compositions. All of these types of polymers are also commercially available.

HPMC is commercially available from the Dow Chemical Company under the brand name Methocel®. HPMC is available in a variety of grades. Most preferred for use in the compositions of the present invention is Methocel E4M, (HPMC 2910), which has a number average molecular weight of approximately 86,000 dalton. The concentration of HPMC in the compositions of the present invention will generally range from 0.05-0.5%, and will preferably be 0.3%.

Guar includes guar gum and guar gum derivatives, such as the hydroxypropyl or hydroxypropyltrimonium chloride derivatives of guar gum. Guar and its derivatives are described in U.S. Pat. No. 6,316,506, the entire contents of which are hereby incorporated by reference. For purposes of the present application, guar includes unsubstituted guar gum and its substituted derivatives. Guar gum and many of its derivatives are commercially available from Rhone-Poulenc (Cranbury, N.J.), Hercules, Inc. (Wilmington, Del.) and TIC Gum, Inc. (Belcamp, Md.). A preferred derivative for use in the compositions of the present invention is hydroxypropyl guar ("HP-Guar"). The concentration of guar in the compositions of the present invention will generally range from 0.01-0.2%, and will preferably be 0.1%.

Carboxyvinyl polymers suitable for use in the present invention are also known as "carbomers" or carboxypolymethylene. They are commercially available from sources such as Noveon, Inc. (Cleveland, Ohio), which distributes them under the trade name Carbopol®. Carbopol polymers are crosslinked, acrylic acid-based polymers. They are cross-linked with allyl sucrose or allylpentaerythritol. Carbopol copolymers are polymers of acrylic acid, modified by $C_{10-30}$ alkyl acrylates, and crosslinked with allylpentaerythritol. A preferred carbomer for use in the compositions of the present invention is a polymer of acrylic acid cross-linked with allyl sucrose or allylpentaerythritol, which is commercially available as Carbopol® 974P. The concentration of carbomer in the compositions of the present invention will generally range from 0.01-0.2%, and will preferably be 0.1%.

HEC is commercially available from Hercules Inc. (Aqualon Division) in a variety of grades, including Natrasol 250 LR, Natrasol 250 MR and Natrasol 250 HR. A preferred HEC for use in the compositions of the present invention is the NF grade material, which is commercially available as Natrasol 250HR. The concentration of HEC in the compositions of the present invention will generally range from 0.05-0.5%, and will preferably range from 0.1-0.2%.

Dextran is commercially available from Amresco in a variety of grades, including Dextran 5, 10, 20, 40, 70, 110, 500, and 2000. A preferred dextran for use in the compositions of the present invention is Dextran 70 (NOC grade; dry powder). The concentration of dextran in the compositions of the present invention will generally range from 0.01-0.2%, and will preferably be 0.1%.

The aqueous compositions of the present invention contain the three specified polymeric ingredients in a ratio ranging from 1:1:1 to 3:3:3, with a ratio of 3:1:1 being most preferred, where the amount of HPMC is listed first and the amounts of the other two polymers are listed second and third, respectively. The total concentration of the three polymeric ingredients should range from 0.1-1%, preferably 0.3-0.9%, and most preferably, 0.4-0.7%.

In addition to the three required polymeric ingredients, the aqueous compositions of the present invention may contain other ingredients as excipients. For example, the compositions may include one or more pharmaceutically acceptable buffering agents, preservatives (including preservative adjuncts), non-ionic tonicity-adjusting agents, surfactants, solubilizing agents, stabilizing agents, comfort-enhancing agents, emollients, pH-adjusting agents and/or lubricants. Preferably, the aqueous composition does not contain any polymeric ingredients, other than the synergistic combination of the three polymeric ingredients specified above, with the exception of polymeric preservatives for compositions that contain a preservative. If the compositions contain a carbomer as one of the three polymers, then the compositions of the present invention do not contain any ionic tonicity-adjusting agents, such as sodium chloride, or other ionic excipients, such as boric acid, as these ingredients have a significant, detrimental effect on the composition's viscosity.

The compositions of the invention have a pH in the range of 5-9, preferably 6.5-7.5, and most preferably 6.9-7.4. If the compositions contain a carbomer as one of the three polymers, it is critical that the compositions are formulated so that the target pH is not exceeded. Once a target pH has been exceeded in compositions containing a carbomer, adding an acid such as hydrochloric acid to adjust the pH downward can compromise the synergistic viscosity. Even relatively small amounts of acid or salts, on the order of 0.005%, can have a significant effect on the viscosity of compositions containing a carbomer.

The compositions of the present invention generally have an osmolality in the range of 220-320 mOsm/kg, and preferably have an osmolality in the range of 235-260 mOsm/kg.

The aqueous compositions of the present invention are suitable for use as artificial tear products to relieve symptoms of dry eye. Alternatively, the compositions of the present invention may act as a vehicle for an ophthalmic drug. Ophthalmic drugs suitable for use in the compositions of the present invention include, but are not limited to: anti-glaucoma agents, such as beta-blockers including timolol, betaxolol, levobetaxolol, carteolol, miotics including pilocarpine, carbonic anhydrase inhibitors, prostaglandins, seretonergics, muscarinics, dopaminergic agonists, adrenergic agonists including apraclonidine and brimonidine; anti-angiogenesis agents; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as EGF; immunosuppressant agents; and anti-allergic agents including olopatadine. The ophthalmic drug may be present in the form of a pharmaceutically acceptable salt, such as timolol maleate, brimonidine tartrate or sodium diclofenac. Compositions of the present invention may also include combinations of ophthalmic drugs, such as combinations of (i) a beta-blocker selected from the group consisting of betaxolol and timolol, and (ii) a prostaglandin selected from the group consisting of latanoprost; 15-keto latanoprost; travoprost; and unoprostone isopropyl. In the case of a cationic drug, the amount of drug and/or the amount of carboxyvinyl polymer and/or the identity and amount of other formulation ingredients may need to be adjusted to minimize or eliminate interactions between the carboxyvinyl polymer and the cationic drug. Preferably, the ophthalmic drug is a neutral or negatively-charged drug.

Although the amount of drug included in the compositions of the present invention will be whatever amount is therapeutically effective and will depend upon a number of factors, including the identity and potency of the chosen drug, the total concentration of drug will generally be about 5% or less.

The compositions of the present invention are preferably not formulated as solutions that undergo a phase transition to a gel upon administration to the eye. The compositions illustrated in the Examples below do not gel upon administration to the eye.

The following examples are presented to illustrate further various aspects of the present invention, but are not intended to limit the scope of the invention in any respect.

EXAMPLES

Example 1

Artificial Tear Composition

A representative formulation for an artificial tear product according to the present invention is shown in Table 1.

TABLE 1

| Ingredients | Concentration (% w/w) |
|---|---|
| HPMC 2910 | 0.3 |
| HP-Guar | 0.1 |
| Carbopol 974P | 0.1 |
| Mannitol | 4.0 |
| NaOH/HCl | qs to pH 7.0 |
| Purified water | qs to 100 |

The composition shown in Table 1 can be prepared by at least two methods. One method involves adding the following ingredients slowly and in the following order to heated purified water (70-80° C.) (approximately 80% of the desired batch volume) with mixing: mannitol, HPMC 2910, Carbopol 974P, and HP-Guar (waiting until each ingredient is mixed well before adding the next). pH is then adjusted with 1N NaOH, and the remaining amount of purified water is added. The composition is then autoclaved at 121° C. for thirty minutes and subsequently cooled to room temperature with constant stirring.

An alternative method of preparing the composition shown in Table 1 is as follows. In a first container, add heated purified water (70-80° C.) (approximately 60% of the desired batch volume), then mix in mannitol, then HPMC 2910, and then Carbopol 974P, waiting until each ingredient is mixed well before adding the next. Autoclave the resulting composition at 121° C. for thirty minutes, then allow the composition to cool to room temperature with constant stirring ("the HPMC/Carbopol composition"). In a separate container, add purified water (approximately 30% of the desired batch volume), then mix in HP-Guar. Adjust the pH of the HP-Guar composition with 1N NaOH to pH 9. Autoclave the HP-Guar composition at 121° C. for thirty minutes, then allow it to cool to room temperature with constant stirring ("the HP-Guar composition"), then aseptically combine the HP-Guar composition with the HPMC/Carbopol composition, and aseptically adjust the final pH to 7.0, if necessary, with 1N NaOH and/or 1N HCl.

Example 2

Synergistic Effect on Viscosity
(HPMC+Guar+Carbomer)

The compositions shown in Table 2 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 2 and in FIG. 1.

TABLE 2

| | Composition (% w/v) | | | | | | | |
|---|---|---|---|---|---|---|---|---|
| Ingredient | 1 | 2 | 3 | 4 | 5 | 6 | 7 | 8 |
| Mannitol | 4.0 | 4.0 | 4.0 | 4.0 | 4.0 | 4.0 | 4.0 | 4.0 |
| HPMC 2910 | — | 0.3 | — | — | 0.3 | 0.3 | — | 0.3 |
| Carbopol 974P | — | — | 0.1 | — | 0.1 | — | 0.1 | 0.1 |
| HP-Guar | — | — | — | 0.1 | — | 0.1 | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 | q.s. 100 |
| Viscosity (cps) | 1.1 | 8.2 | 488.1 | 5.3 | 1339.5 | 32.3 | 1273.0 | 2477.0 |
| Subst. Synergy@ | — | — | — | — | — | — | — | Yes |

@Subst. Synergy = substantial synergy: greater than 150% of the simple sum of the three respective single polymer solutions

Example 3

Synergistic Effect on Viscosity
(HPMC+HEC+Guar; HPMC+HEC+Carbomer)

The compositions shown in Table 3 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 3.

TABLE 3

| Ingredient | Composition (% w/v) | | | | | | | | | |
|---|---|---|---|---|---|---|---|---|---|---|
| | 9 | 10 | 11 | 12 | 13 | 14 | 15 | 16 | 17 | 18 |
| Mannitol | 4.0 | 4.0 | 4.0 | 4.0 | 4.0 | 4.0 | 4.0 | 4.0 | 4.0 | 4.0 |
| HPMC 2910 | — | 0.3 | — | — | — | 0.3 | — | — | 0.3 | 0.3 |
| HP-Guar | — | — | 0.1 | — | — | — | 0.1 | — | 0.1 | — |
| Carbopol 974P | — | — | — | 0.1 | — | — | — | 0.1 | — | 0.1 |
| Natrasol 250HR | — | — | — | — | 0.1 | 0.1 | 0.1 | 0.1 | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 | q.s. 100 | q.s. 100 | q.s. 100 |
| Viscosity (cps) | 1.0 | 8.0 | 5.2 | 465.9 | 3.0 | 27.7 | 10.9 | 642.0 | 62.8 | 1300.5 |
| Subst. Synergy@ | — | — | — | — | — | — | — | — | Yes | Yes |

@Subst. Synergy = substantial synergy: greater than 150% of the simple sum of the three respective single polymer solutions Example 4

Lack of Synergistic Effect on Viscosity (Polyvinyl Alcohol+Chondroitin Sulfate+Polyvinylpyrrolidone)

The compositions shown in Table 4 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 4. Airvol 523S is a commercially available polyvinyl alcohol polymer. Chondroitin sulfate is a commercially available polymer. K90 is a commercially available polyvinylpyrrolidone polymer.

Example 5

Lack of Synergistic Effect on Viscosity (Polyvinyl Alcohol+Chondroitin Sulfate+Carbomer; Polyvinyl Alcohol+Polyvinylpyrrolidone+Carbomer; Chondroitin Sulfate+Polyvinylpyrrolidone+Carbomer)

The compositions shown in Table 5 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 5. Airvol 523S is a commercially available polyvinyl alcohol polymer. Chondroitin sulfate is a commercially available polymer. K90 is a commercially available polyvinylpyrrolidone polymer.

TABLE 4

| Ingredient | Composition (% w/v) | | | | | | | |
|---|---|---|---|---|---|---|---|---|
| | 19 | 20 | 21 | 22 | 23 | 24 | 25 | 26 |
| Mannitol | 4.0 | 4.0 | 4.0 | 4.0 | 4.0 | 4.0 | 4.0 | 4.0 |
| PVA (Airvol 523S) | — | 0.2 | — | — | 0.2 | 0.2 | — | 0.2 |
| Chondroitin Sulfate | — | — | 0.2 | — | 0.2 | — | 0.2 | 0.2 |
| PVP (K90) | — | — | — | 0.2 | — | 0.2 | 0.2 | 0.2 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 | q.s. 100 |
| Viscosity (cps) | 1.0 | 1.5 | 1.3 | 1.4 | 1.7 | 1.9 | 1.8 | 2.3* |
| Subst. Synergy@ | — | — | — | — | — | — | — | No |

*slight, transparent precipitate observed
@Subst. Synergy = substantial synergy: greater than 150% of the simple sum of the three respective single polymer solutions The viscosities of the single polymer solutions for polyvinyl alcohol, chondroitin sulfate and polyvinylpyrrolidone can be found in Table 4—Examples 20-22.

TABLE 5

| Ingredient | Composition (% w/v) | | | | | | |
|---|---|---|---|---|---|---|---|
| | 27 | 28 | 29 | 30 | 31 | 32 | 33 |
| Mannitol | 4.0 | 4.0 | 4.0 | 4.0 | 4.0 | 4.0 | 4.0 |
| PVA (Airvol 523S) | — | 0.2 | — | — | — | 0.2 | 0.2 |
| Chondroitin Sulfate | — | — | 0.2 | — | 0.2 | 0.2 | — |
| PVP (K90) | — | — | — | 0.2 | 0.2 | — | 0.2 |
| Carbopol 974P | 0.1 | 0.1 | 0.1 | 0.1 | 0.1 | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 |
| Viscosity (cps) | 441.6 | 323.8 | 12.7 | N/A* | 16.7** | 14.2 | N/A* |
| Subst. Synergy@ | — | — | — | — | — | No | No |

*PVP was incompatible with Carbopol 974P - it formed a precipitate.
**Solution obtained only by specific order of mixing: mannitol, then chondroitin sulfate, then PVP, then carbomer.
@Subst. Synergy = substantial synergy: greater than 150% of the simple sum of the three respective single polymer solutions Example 6

Synergistic Effect on Viscosity
(HPMC+HEC+Guar; HPMC+HEC+Carbomer)

The compositions shown in Table 6 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 6.

Example 7

The Effect of Polymer Ratio on Viscosity

The effect of polymer ratio on viscosity was determined by preparing compositions containing a ratio of the three designated polymers that varied from 1:1:1 to 3:3:3. The compositions are shown in Table 5. The viscosity was determined using a Bohlin Rheometer Model CS-10 at 25° C. (shear rate: 0.8 1/s). Two people independently prepared the indicated compositions and determined viscosity values (n=10 for each person). The averages of the results are shown in Table 7.

TABLE 6

| Ingredient | Composition (% w/v) | | | | | | | | | |
|---|---|---|---|---|---|---|---|---|---|---|
| | 34 | 35 | 36 | 37 | 38 | 39 | 40 | 41 | 42 | 43 |
| Mannitol | 4.0 | 4.0 | 4.0 | 4.0 | 4.0 | 4.0 | 4.0 | 4.0 | 4.0 | 4.0 |
| HPMC 2910 | — | 0.3 | — | — | — | 0.3 | — | — | 0.3 | 0.3 |
| HP-Guar | — | — | 0.1 | — | — | — | 0.1 | — | 0.1 | — |
| Carbopol 974P | — | — | — | 0.1 | — | — | — | 0.1 | — | 0.1 |
| Dextran 70 | — | — | — | — | 0.1 | 0.1 | 0.1 | 0.1 | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 | q.s. 100 | q.s. 100 | q.s. 100 |
| Viscosity (cps) | 1.1 | 7.9 | 5.2 | 461.6 | 1.4 | 8.4 | 5.2 | 379.3 | 46.1 | 829.2 |
| Subst. Synergy@ | — | — | — | — | — | — | — | — | Yes | Yes |

@Subst. Synergy = substantial synergy: greater than 150% of the simple sum of the three respective single polymer solutions

TABLE 7

| Ingredient | Composition (% w/v) | | | | |
|---|---|---|---|---|---|
| | 44 | 45 | 46 | 47 | 48 |
| Mannitol | 4.0 | 4.0 | 4.0 | 4.0 | 4.0 |
| HPMC 2910 | 0.1 | 0.1 | 0.1 | 0.3 | 0.3 |
| Carbopol 974P | 0.1 | 0.1 | 0.3 | 0.1 | 0.3 |
| HP-Guar | 0.1 | 0.3 | 0.1 | 0.1 | 0.3 |
| NaOH/HCl | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 |
| Polymer ratio HPMC:Carbopol:HP-Guar | 1:1:1 | 1:1:3 | 1:3:1 | 3:1:1 | 3:3:3 |
| Viscosity (cps) [Stnd. Deviation] | 2865 [700] | 8450 [1655] | 101950 [2899] | 3660 [141] | 145000 [1414] |

Example 8

Effect of Salt on Viscosity for a Polymer Combination that Contains Carbomer

The compositions shown below in Table 8 were prepared to determine the effect of the addition of salt (NaCl) on viscosity. The viscosity of each sample was determined using a Brookfield cone/plate viscometer (52 cone, 3 rpm). The results are shown in Table 8.

TABLE 8

| INGREDIENT | Composition (% w/v) | | | | |
|---|---|---|---|---|---|
| | Ex. 1 | X | Y | Z | AA |
| Mannitol | 4.0 | 4.0 | 4.0 | 4.0 | 4.0 |
| HPMC 29.0 | 0.3 | 0.3 | 0.3 | 0.3 | 0.3 |
| Carbopol 974P | 0.1 | 0.1 | 0.1 | 0.1 | 0.1 |
| HP Guar | 0.1 | 0.1 | 0.1 | 0.1 | 0.1 |
| NaCl | 0 | 0.001 | 0.005 | 0.01 | 0.05 |
| NaOH/HCl | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 |
| Viscosity (cps) | 1569 | 1382 | 774 | 608 | 202 |

Example 9

Effect of Boric Acid on Viscosity for a Polymer Combination that Contains Carbomer The compositions shown below in Table 9 were prepared to determine the effect of the addition of boric acid on viscosity. The viscosity of each sample was determined using a Brookfield cone/plate viscometer (52 cone, 3 rpm). The results are shown in Table 9.

TABLE 9

| INGREDIENT | Composition (% w/v) | | | | |
|---|---|---|---|---|---|
| | Ex. 1 | X | Y | Z | AA |
| Mannitol | 4.0 | 4.0 | 4.0 | 4.0 | 4.0 |
| HPMC 2910 | 0.3 | 0.3 | 0.3 | 0.3 | 0.3 |
| Carbopol 974P | 0.1 | 0.1 | 0.1 | 0.1 | 0.1 |
| HP Guar | 0.1 | 0.1 | 0.1 | 0.1 | 0.1 |
| Boric acid | 0 | 0.001 | 0.005 | 0.01 | 0.05 |
| NaOH/HCl | q.s. pH 7 | q.s. pH 7 | q.s. pH 7 | q.s. pH 7 | q.s. pH 7 |
| Purified Water | q.s. 100 | q.s. 100 | q.s. 100 | q.s. 100 | q.s. 100 |
| Viscosity (cps) | 1250 | 1035 | 682 | 531 | 172 |

Example 10

Effect of Total Polymer Concentration on Viscosity

Figure 2:
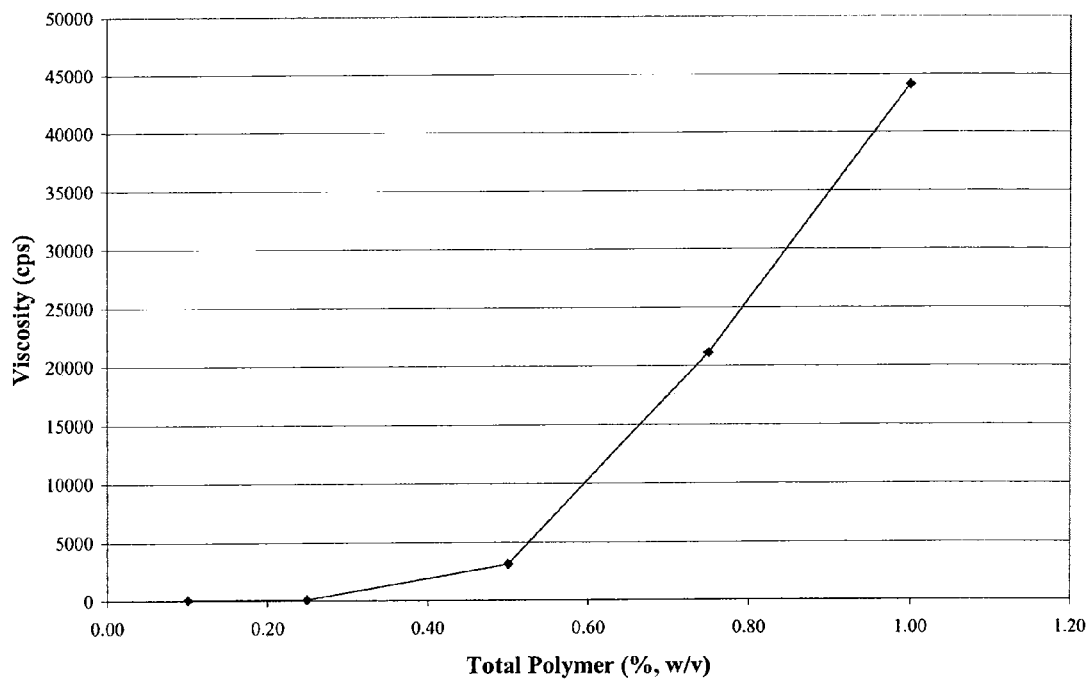
FIG. 2 shows the effect of total polymer concentration on viscosity for the three polymer system of hydroxypropyl methylcellulose, guar gum and carboxyvinyl polymer for a concentration ratio of 3:1:1 (hydroxypropyl methylcellulose:guar gum:carboxyvinyl polymer) at pH 7.0.

The effect of total polymer concentration on the viscosity of compositions containing a combination of HPMC 2910, HP-Guar and Carbopol 974P was evaluated using 5 compositions containing only the three designated polymers, mannitol and purified water. In each case, the composition contained 4.0% (w/w) of mannitol and had an adjusted pH of 7.0. The total polymer concentrations ranged from 0.1 to 1.0, with the ratio of polymers held constant at 3:1:1 (HPMC:HP-Guar:Carbopol). The viscosity was determined using a Bohlin Rheometer Model CS-10 at 25° C. (shear rate: 0.8 1/s). The results (average of 10 measurements, n=10) are shown in Table 10 and FIG. 2.

TABLE 10

| Total Polymer Concentration (% w/v) | Viscosity (cps) |
| --- | --- |
| 0.1 | 48 |
| 0.25 | 83 |
| 0.5 | 3087 |
| 0.75 | 21,099 |
| 1.0 | 44,064 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of alleviating the symptoms of dry eye comprising topically administering to the eye an aqueous composition comprising three polymeric ingredients having a synergistic effect on the composition's viscosity wherein the three polymeric ingredients are hydroxypropyl methylcellulose and a combination of two polymers selected from the group of combinations consisting of guar gum and a carboxyvinyl polymer; hydroxyethyl cellulose and a carboxyvinyl polymer; and dextran and a carboxyvinyl polymer, provided that the composition does not contain sodium chloride or boric acid wherein the total concentration of the three polymeric ingredients ranges from 0.1-1% (w/v).

2. The method of claim 1 wherein the guar gum ingredient is hydroxypropyl guar.

3. The method of claim 1 wherein the carboxyvinyl polymer is a polymer of acrylic acid crosslinked with allyl sucrose or allylpentaerythritol.

4. The method of claim 1 wherein the total concentration of the three polymeric ingredients ranges from 0.3-0.9% (w/v).

5. The method of claim 1 wherein the composition consists essentially of hydroxypropyl methylcellulose; a carboxyvinyl polymer; hydroxypropyl guar; and mannitol, wherein the total concentration of the three polymeric ingredients ranges from 0.1-1%(w/v), the composition has a pH of 6.5-7.5 and an osmolality in the range of 235-260 mOsm/kg.

\* \* \* \* \*